(12) United States Patent
Smalling

(10) Patent No.: US 6,730,119 B1
(45) Date of Patent: May 4, 2004

(54) PERCUTANEOUS IMPLANTATION OF PARTIALLY COVERED STENTS IN ANEURYSMALLY DILATED ARTERIAL SEGMENTS WITH SUBSEQUENT EMBOLIZATION AND OBLITERATION OF THE ANEURYSM CAVITY

(75) Inventor: Richard W. Smalling, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 139 days.

(21) Appl. No.: 09/680,859

(22) Filed: Oct. 6, 2000

(51) Int. Cl.$^7$ ................................................. A61F 2/06
(52) U.S. Cl. .................... 623/1.35; 623/1.15; 623/1.11; 623/1.23; 606/194
(58) Field of Search .............................. 427/2, 24, 2.25; 623/1.1, 1.11, 1.13, 1.15, 1.16, 1.18, 1.2, 1.23, 1.3, 1.31, 1.34, 1.35, 1.42–1.44, 1.46, 11.11, 23.7, 12; 606/191, 192, 194, 195, 198

(56) References Cited

U.S. PATENT DOCUMENTS

| | | | |
|---|---|---|---|
| 5,507,769 A | 4/1996 | Marin et al. | 606/198 |
| 5,562,724 A | 10/1996 | Vorwerk et al. | 623/1 |
| 5,591,228 A | 1/1997 | Edoga | 623/1 |
| 5,609,627 A | 3/1997 | Goicoechea et al. | 623/1 |
| 5,669,924 A | 9/1997 | Shaknovich | 606/108 |
| 5,693,087 A | 12/1997 | Parodi | 623/1 |
| 5,695,517 A | 12/1997 | Marin et al. | 606/198 |
| 5,716,365 A | 2/1998 | Goicoechea et al. | 606/108 |
| 5,718,724 A | 2/1998 | Goicoechea et al. | 623/1 |
| 5,720,735 A | 2/1998 | Dorros | 604/284 |
| 5,749,825 A | 5/1998 | Fischell, III | 600/3 |
| 5,843,160 A | 12/1998 | Rhodes | 623/1 |
| 5,916,263 A | 6/1999 | Goicoechea et al. | 623/1 |
| 5,938,696 A | 8/1999 | Goicoechea et al. | 623/1 |
| 5,961,548 A | 10/1999 | Shmulewitz | 623/1 |
| 5,968,069 A | 10/1999 | Dusbabek et al. | 606/194 |
| 6,070,589 A * | 6/2000 | Keith et al. | 128/898 |
| 6,090,128 A * | 7/2000 | Douglas | 623/1.11 |
| 6,524,336 B1 * | 2/2003 | Papazolgou et al. | 623/1.35 |
| 2001/0004707 A1 * | 6/2001 | Dereume et al. | 623/1.16 |
| 2002/0156521 A1 * | 10/2002 | Ryan et al. | 623/1.13 |

OTHER PUBLICATIONS

Feinglass, Joe, et al., "Late survival risk factors for abdominal aortic aneurysm repair: Experience from fourteen Department of Veterans Affairs hospitals." *Surgery*, Jul. 1995 (pp. 16–23).

(List continued on next page.)

*Primary Examiner*—David J. Isabella
*Assistant Examiner*—Urmi Chattopadhyay
(74) *Attorney, Agent, or Firm*—Mark R. Wisner; Malcolm H. Skolnick

(57) ABSTRACT

A low profile, abdominal aortic aneurysm exclusion device with iliac vessel extensions. A sectional, bifurcated stent forms part of an endoluminal prosthesis to eliminate or reduce the risk of rupture of aortic aneurysms. An apparatus and a method for introducing the bifurcated stent in sections into the vasculature and assembling the sections in situ to form a "scaffold" for introduction of material to re-endothelialize and/or occlude the aneurysm cavity. After trans-stent embolization of the aneurysm cavity with thrombogenic material, laminar flow stimulates endothelialization of the stent lumen. Subsequent organization and fibrosis of the persistent thrombus reinforces the wire-mesh or etched metal tubular scaffold comprising the stent and serves to stabilize and shrink the aneurysm. A single stent deployed with the same method may be used in non-bifurcated vessels.

8 Claims, 6 Drawing Sheets

OTHER PUBLICATIONS

Blum, Ulrich, et al., "Endoluminal Stent–Grafts for Infrarenal Abdominal Aortic Aneurysms." *The New England Journal of Medicine*, vol. 336, No. 1, Jan. 2, 1997 (pp. 13–20).

Dyet, J.F., "Pictorial Review: Endovascular Repair of Abdominal Aortic Aneurysms." *The British Journal of Radiology*, 69, Nov. 1996 (pp. 1069–1074).

Ruiz, Carlos E., et al., "A Novel Method for Treatment of Abdominal Aortic Aneurysms Using Percutaneous Implantation of a Newly Designed Endovascular Device." Presented in part at the 67th Annual Scientific Sessions of the American Heart Association, Dallas, Texas, Nov. 1994.

White, Geoffrey H., et al., "Historic Control Comparison of Outcome for Matched Groups of Patients Undergoing Endoluminal Versus Open Repir of Abdominal Aortic Aneurysms." *Journal of Vascular Surgery*, Feb. 1996 (pp. 201–212).

Ruiz, Carlos E., et al., "Percutaneous Treatment of Abdominal Aortic Aneurysm in a Swine Model: Understanding the Behavior of Aortic Aneurysm Closure Through a Serial Histopathological Analysis." Presented in part at the 69th Scientific Sessions of the American Heart Association, New Orleans, Louisiana, Nov. 1996 and published in abstract form (*Circulation*, 1996;95[suppl I]:I–59).

\* cited by examiner

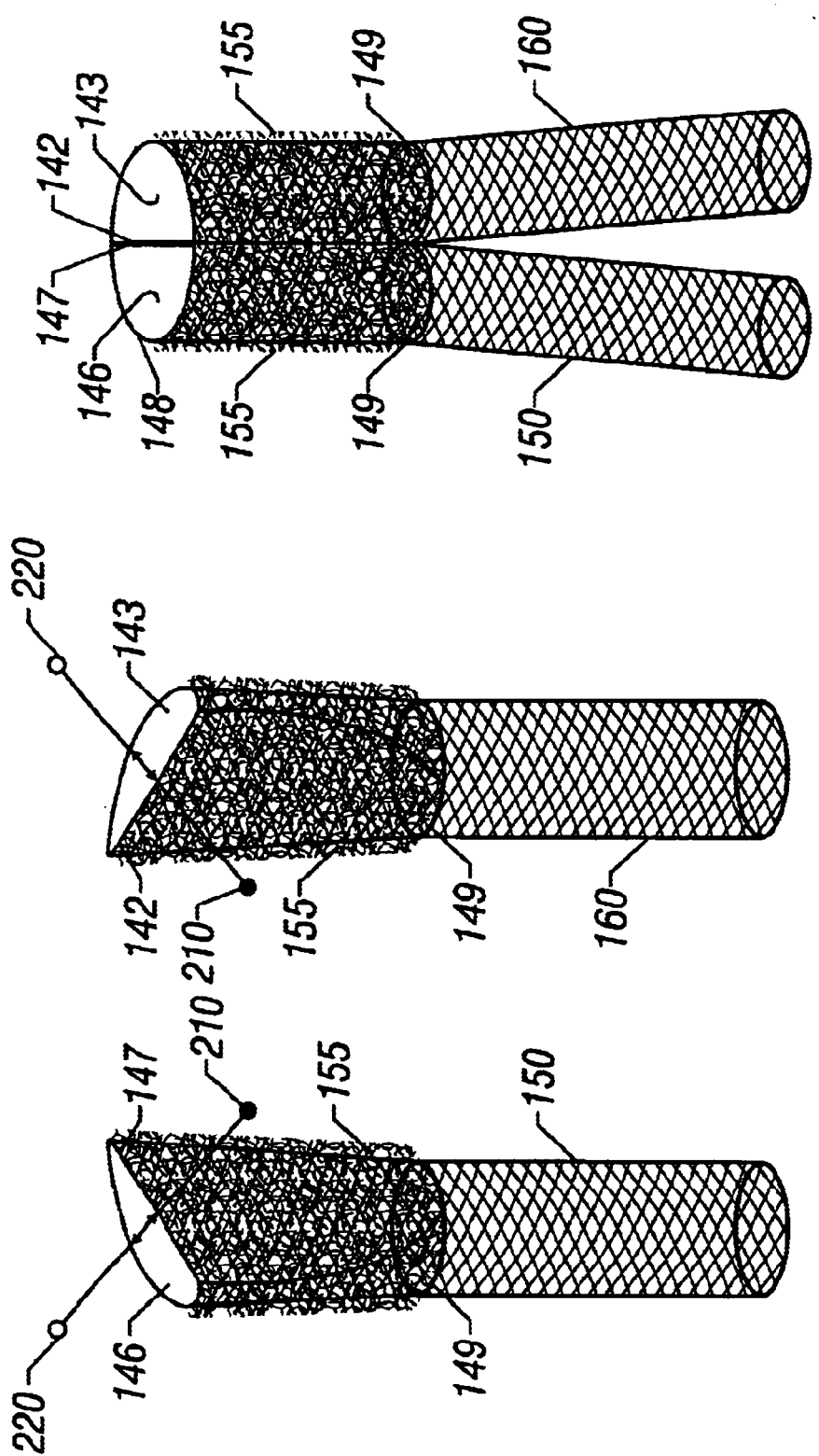

PERCUTANEOUS IMPLANTATION OF PARTIALLY COVERED STENTS IN ANEURYSMALLY DILATED ARTERIAL SEGMENTS WITH SUBSEQUENT EMBOLIZATION AND OBLITERATION OF THE ANEURYSM CAVITY

BACKGROUND OF THE INVENTION

A stent is used to provide a prosthetic intraluminal wall, e.g., in the case of a stenosis to provide an unobstructed conduit for blood through the area of the stenosis. An endoluminal prosthesis comprises a stent which carries a prosthetic graft layer of fabric or other material and is used in the instant invention to treat an aneurysm by removing the pressure on a weakened part of an artery so as to reduce the risk of distal embolization or rupture of the distended wall of the aneurysm.

Typically, a stent or endoluminal prosthesis is implanted in a blood vessel at the site of the aneurysm by minimally invasive techniques in which the stent is compressed along its long axis and is delivered by catheter to the site where it is required. A cut down technique in which the blood vessel to be used as conduit is exposed by minor surgical means. Various catheters or sheaths are inserted through small openings made in the conduit blood vessel. The stent is directed into the correct position and the catheter is withdrawn. The catheter's withdrawal allows the stent to re-expand to a predetermined diameter in the vessel.

Aneurysms in vessel walls at or near bifurcations pose additional problems because the intraluminal support provided by the stent must extend from the main vessel into both branches of the bifurcation. This requirement complicates the procedures for introducing the catheters for positioning the stent(s), as well as insertion and placement of the stent components to conform to the configuration of the bifurcation. Stent branches must be joined with the main stent in the correct configuration and without leakage at any juncture. It is also desirable to conduct additional procedures to thrombose the material in the aneurysm cavity and to ensure re-endotheliazation of the stent walls.

A number of prostheses are known for treating the formation of aneurysms in bifurcated body lumens. A typical previously practiced bifurcated prosthesis comprises a hollow tubular graft having a main section and first and second legs or extensions. For example, in open surgery to repair an abdominal, aortic aneurysm, the main section of the prosthesis is sutured to the aorta below the renal arteries, and the first and second branches of the graft are sutured to the corresponding iliac arteries. Surgical implantation of known prostheses poses a major risk of mortality and morbidity, and open surgical implantation frequently cannot be performed on patients in poor health.

Even if surgery is deemed of acceptable risk, the cumulative mortality of patients with spontaneous rupture of abdominal aortic aneurysms is approximately seventy-five percent (75%), despite emergency surgical treatment. The likelihood of rupture is under five percent in aneurysms less than 5 cm in diameter; however, in aneurysms larger than this, surgery is required to reduce the risk of spontaneous rupture and hemorrhage. The mortality of such surgery ranges between four and eight percent (4–8%). The highest risk occurs in patients greater than sixty-nine (69) years of age with chronic obstructive pulmonary disease, left ventricular hypertrophy or a history of cerebral vascular disease. In an attempt to lower the mortality of aneurysm repair, percutaneous treatment of aortic aneurysms has been attempted. Attempts using covered stent grafts to treat the aneurysm have been approximately eighty-five percent (85%) successful. Some patients undergoing this procedure require conversion in open surgical operations. Other serious complications occur in approximately ten percent (10%) of the patients so treated. Many of these patients develop a post implantation syndrome consisting of leukocytosis and elevated C-reactive protein levels. Other difficulties with covered stent grafts include difficulty in placement of the grafts, potential for obliteration of branch vessel ostia with the stent graft which in turn might compromise flow to lumbar or visceral arteries.

In attempts to overcome the drawbacks associated with surgically implanted grafts, a number of methods and devices have been developed to implant such grafts percutaneously. Komberg, U.S. Pat. No. 4,562,596 describes a bifurcated graft for intraluminal, percutaneous implantation. The graft comprises a hollow tubular main portion connected to a first leg and a shorter second leg. The main portion includes a plurality of barbs that impale the healthy tissue of the aorta to maintain the graft in position. Such grafts have a drawback in their inability to provide a fluid tight seal at the ends of the graft. Without adequate sealing, bypass flow paths (endo leaks) may develop between the graft and the aneurysm wall, which may eventually cause rupture of the aneurysm.

Chuter, U.S. Pat. No. 5,387,235 describes a bifurcated graft having a main portion connected to first and second legs. The main portion, first and second legs each include a barbed self-expanding anchor ring that engages healthy tissue in either the aorta or the iliac arteries to retain the graft in position. These types of devices have a drawback that the diameter of the delivery system must be large enough to accommodate the combined diameters of each of the anchor deployment mechanisms. Thus, it may not be possible to use the device taught in the Chuter '235 patent in patients having small diameter femoral or iliac arteries.

Yet another drawback of previously known bifurcated grafts is the difficulty encountered in pulling the legs of the graft into the branch vessels. While a number of methods have been described in the prior art for accomplishing this task, these methods generally involve snaring a guide wire, either in the iliac artery or in the abdominal aorta, to place a guide wire for deploying the leg of the graft in the contralateral branch.

Shmulewitz, U.S. Pat. No. 5,961,548 describes a bifurcated graft, and methods of implantation that provide positive sealing between the graft and healthy tissue proximal and distal of the graft site. Shmulewitz further describes methods of implantation of a bifurcated graft that enable smaller diameter delivery systems to be employed than are taught in the prior art as well as enhancement of the ease with which the legs of the graft may be deployed in the branches of a bifurcated body lumen.

The drawback presented in the graft and methods taught in Shmulewitz '548 is that the stent graft is covered, which has four major problems:

(1) Covered stent grafts are 22 F or greater and must be inserted by surgical cutdown due to the obligate nature of increased bulkiness of a stent covering combined with the metallic substrate being incompressible and, therefore, unable to be compressed below 22 F.

(2) Covering the stent graft completely eliminates blood flow to the side branches, such as the lumbars from the central lumen. This elimination of blood flow has produced paraplegia in animal models. However, retrograde collateral flow from the lumbars is not prevented. This leads to endo leaks with the potential for aneurysm expansion in humans who have been implanted with similar devices.

(3) In patients with short cuffs of normal aorta below the renal arteries, completely covered stent grafts are not able to achieve secure placement and are therefore prone to dislodgment and axial migration with subsequent endo leaking and aneurysm expansion and rupture.

(4) The second covered stent graft is designed to dock minimally within the first. There are several other similar designs, which have a very high incidence of left iliac side branch graft dissociation in time due to healing and/or expansion of the aneurysm. This disassociation of the left iliac side branch portion from the main graft results in leakage of blood into the aneurysm cavity, further expansion of the aneurysm and late, often fatal, aneurysm rupture.

Rhodes, U.S. Pat. No. 5,843,160, describes expandable, intraluminal prosthesthes for the treatment of aneurysmal or occlusive disease at a bifurcation of a vessel, duct or lumen. Each prosthesis taught by Rhodes includes three expandable sleeve sections which are arranged to be located in respective portions of the vessel, duct or lumen contiguous with the bifurcation and secured together in situ. The Rhodes prosthesis for aorto-iliac aneurysmal disease includes a common, stent supported sleeve section having an expandable outer balloon for engaging and trapping the thrombus in the aneurysmal space in the abdominal aorta, and a pair of stent-supported sleeve limb sections. The limb sections are connected to the common section to provide a passage for blood to flow through the prostheses. One or more of the limb sections can also include an outer balloon for engaging the thrombus within its associated aneurysmal space. Sealing mesh is provided on the prosthesis to prevent the egress of emboli and to permanently secure it in place. The Rhodes prosthesis for aorto-iliac occlusive disease is similar to the prosthesis for aneurysmal disease, except that the sections of the prosthesis do not include an outer balloon. The invention described by Rhodes presents several problems:

(1) The device is bulky, including at least four superimposed layers with inner stent rings, an outside fabric covering, balloon material external to this fabric covering, and subsequently mesh or other thrombogenic material covering the balloon. This degree of bulkiness may preclude percutaneous delivery and requires surgical interventions for insertion.

(2) The external balloon feature of this design is particularly problematic. In other applications with permanently implanted balloons (such as embolization balloons for treating large arterial venous malformations) the balloon material degrades and ruptures after several months to years post implant. Such an occurrence in this situation would be disastrous and would likely lead to further aneurysm, expansion, and rupture.

(3) Simply placing mesh or fibers in a potential space has not produced thrombosis and fibrosis of the aneurysm cavity in humans. This space must be almost completely filled with thrombogenic material for the progressive thrombosis and fibrosis to occur.

(4) This covered stent design precludes placement in patients with a short cuff of normal aorta below the renal ostia.

(5) This stent graft will lack axial stability due to the fact that the stent segments are interspersed throughout the fabric graft. The fabric will then be prone to collapsing upon itself axially without support of a continuous stent within it to form a backbone.

(6) In human applications of similar devices, axial dislodgment also produces a significant incidence of endo leaks, further aneurysm expansion, and rupture.

Fischell, U.S. Pat. No. 5,749,825, discloses a system designed for treatment of coronary artery stenoses, not aortic aneurysms. It has no provision for exclusion of the aneurysm cavity. Treatment of bifurcation coronary disease is already readily accomplished using conventional balloon expandable stent systems.

Dorros, U.S. Pat. No. 5,720,735, discloses a device designed for treatment of stenotic or occlusive vascular disease in bifurcated segments. There are no implications for its use in aneurysmal disease as taught by the instant invention, particularly with regard to occlusion of the aneurysm cavity.

Goicoechea el al., U.S. Pat. No. 5,718,724, describes a covered stent graft for treatment primarily of aortic aneurysm and bifurcation aortic aneurysm disease. Problems with this device include:

(1) This device is designed to be deployed just below the renal arteries without retention hooks, thus allowing for axial dislodgment in the case of short necks of normal aorta immediately below the renal artery ostia. Without a direct application mechanism, and without adequate axial stability, this graft will have a tendency to suffer axial dislodgment with subsequent endo leaks, aneurysm expansion, and rupture.

(2) The links in the stent material are not constructed from a solid tube and thus are prone to late fracture with subsequent penetration of the graft material which would permit leakage of blood into the aneurysm cavity, aneurysm expansion, and late rupture.

(3) The short overlap segment of the bifurcation segments. Lack of positioning of the bifurcation segments at the aortic bifurcation leads to significant axial instability of the bifurcation segments and late disruption of the junction with leakage of blood into the aneurysm cavity, aneurysm expansion, and late aneurysm rupture. Similar devices have suffered significant incidences of late aneurysm rupture due to the above mentioned design issues.

Parodi, U.S. Pat. No. 5,693,087, discloses a device designed as a composite of a proximal stent bonded to traditional tubular vascular grafting material such as DACRON®. Problems with this device include:

(1) There is no internal stent structure, which allows the potential for axial migration.

(2) The proximal stent is not designed to cover the renal ostia; therefore, positioning this stent in patients with short necks below the renal arteries can be problematic and prone to axial migration and endoluminal leakage.

(3) The bulkiness of the device precludes percutaneous delivery and it must be inserted using surgical cutdown techniques.

(4) The commercial version most commonly utilized is not bifurcated and therefore the contralateral iliac is excluded from blood flow within the stent. This exclusion necessitates coil embolization of the contralateral vessel, followed by a surgical femoral-femoral bypass to the contralateral iliac, which is decidedly invasive.

(5) Further difficulty with deployment of this device is the necessity for stopping the heart during proximal stent expansion to prevent axial migration. While in most cases this can be done with intravenous adenosine without sequelae, significant potential risk does exist with this maneuver.

Marin, U.S. Pat. No. 5,695,517, discloses a bifurcation stent graft utilizing separate bifurcation limbs. The graft material is sewn to stents, which are subsequently manually formed into a "D" type configuration. Problems with this device include:

(1) The device is bulky and cannot be delivered percutaneously. It must be delivered by insertion by surgical incision and repair.

(2) Since the graft material does not have continuous stent support, there is a considerable degree of axial instability. The short stent segment requires a long segment of normal aorta prior the aneurysm, below the renal arteries, for deployment and there is no provision for above renal artery deployment.

(3) Since the grafts are independent, slight slippage of either limb of the graft produces a major disruption of the mechanical connection between them, which is largely frictionally based. This disruption potentially leads to a major endoluminal leak, aneurysm expansion, and rupture.

(4) The "D" type configuration is achieved by use of a mechanical linkage device rather than self-expansion of preformed "D" segments. Furthermore, the "D" segment is just below the renal arteries rather than at the bifurcation and it is not constrained by an external main stent. Therefore, mechanically, it is significantly unstable.

Marin et al., U.S. Pat. No. 5,507,769. This patent is similar to the previous Marin Pat. No. 5,695,517 and presents similar limitations and/or disadvantages including:

(1) The short stent segment proximally precludes axial stability since the renal vessels cannot be crossed with this device.

(2) The lack of continuous stent material, proximally to distal, leads to further axial instability. Axial displacement of the graft would lead to massive endo leak, aneurysm expansion, and rupture.

(3) The covered, non-permeable nature of the graft material could exclude side branches, providing further pressurization of the aneurysm cavity from the side branches, but, in addition, limiting antegrade blood flow through the side branches, which may lead to lumbar ischemia.

(4) The semi-circular proximal segment is by definition in a tapered area of the aorta and, therefore, cannot achieve sufficient axial stability to maintain its position. It also has no longitudinal tapering which would help in preventing axial displacement.

Edoga, U.S. Pat. No. 5,591,228, teaches a device requiring insertion through a surgical incision, including left subclavian artery and bilateral femoral arteries. The device entails graft material adherent to loose, large cell stents inside the proximal distal portions of the graft material. Problems include:

(1) This device is bulky and cannot be inserted percutaneously.

(2) It has poor axial stability since the proximal and distal limbs are fixed by stents, but there is loose graft material between the stents.

(3) It will not be applicable for patients with small aneurysm necks below the renal arteries, or short aneurysm necks below the renal arteries.

(4) The risk of graft material perforation secondary to fatigue fracture of the loose stent struts is excessive. This perforation could subsequently result in aneurysm expansion and late rupture.

Vorwerk et al., U.S. Pat. No. 5,562,724, discloses a design consisting of a porous bag attached to a proximal ring stent. The bag is non-penetrable to blood and, therefore, cannot be crossed to embolize the surrounding aneurysm cavity. Problems with this design include:

(1) This design allows for poor axial stability given the short stent segment and the covered design therefore precluding placement above the renal arteries. Therefore, aneurysms with short necks will have a very short space for stabilization of the proximal portion. Axial migration will be prone to occur with subsequent severe endo leak, aneurysm expansion, and late rupture.

(2) The legs are covered stents. The wires that are used to insert these legs are not angled and, therefore, they have potential for kinking within the main proximal stent. The non-permeable nature of this device, as described in the '724 patent, predisposes it to significant endo leaks from the lumbars as well as potentially from the iliac vessels.

Shaknovich, U.S. Pat. No. 5,669,924, describes a Y-stent/shuttle delivery system designed for use in treatment of atherosclerotic bifurcation disease in relatively small vessels. To be applicable for aortic aneurysm applications it would have to be delivered from a superior approach. The size necessary for such a device would exceed the available access size for superior delivery, such as the brachial artery. Therefore, this device would be limited to treating atherosclerotic obstructions in small-to-medium size vessels, significantly smaller than the aortic bifurcation, and would have no utility for treatment of aortic aneurysms. Similarly, there is no provision for occluding blood flow into aneurysm cavities should it be modified for treatment of aortic aneurysms.

SUMMARY OF THE INVENTION

To overcome the disadvantages and limitations of the prior art, the present invention provides a main wire mesh stent or scaffold for placement in the lumen of a blood vessel with an aneurysm at or near a bifurcation in the vessel. A particular example of the invention may be used in the abdominal aorta in patients with an abdominal aortic aneurysm. DACRON® tufts, bio-compatible foam or gel are bonded to the external surface of the stent to stimulate thrombosis of the aneurysm cavity and endothelialization of the graft lumen. Radio-opaque markers delineate the margins of the partially covered regions on the stent and assist in placement of the elements of the stent in the appropriate position in the vessel proximate to the location of the aneurysm. The present invention also comprises two bifurcation segments, or stents, comprised of a memory retentive material that is compressible to a first shape for insertion into the vessel and subsequent expansion in a position that substantially overlaps with and fits tightly within the main stent, with a larger profile above the bifurcation, acting like a "cork" to resist displacement and/or subsequent disassociation of the bifurcation stents. Each of the bifurcation stents that comprise the present invention are configured in a semi-circular, half-cork type of configuration that is tapered at the level of the bifurcation to give the stent a frustroconical shape with the larger, proximal end being the end that expands into contact with the inside wall of the main stent, thereby preventing axial displacement.

Variable cell sizes (openings in the stent wall) are utilized to minimize obstruction to side branch flow proximally (at the level of the renal arteries) and to maximize internal laminar flow distal to the renal arteries. Tapered, semi-circular, proximal orifices on the bifurcation stent elements optimize in-flow proximally and facilitate proximation and juncture with the main stent. Distally, the stents expand to a tubular conformation, thus maximizing contact with the iliac lumens.

Angled guide-wires with marker bands are used to position the bifurcation stents and direct their deployment. Radio-opaque markers on the bifurcation deployment sheath are used to insure proper alignment of the bifurcation stent elements. Trans-stent placement of vascular occlusion coils, polymeric foams, gels or glues stimulates closure of the aneurysm cavity external to the stent assembly. The small sheath size allows percutaneous closure of the vascular access sites in most patients, further reducing risks for bleeding complications, reducing both morbidity and time to ambulation.

In a preferred method in accordance with the present invention, the delivery of coils, or other thrombogenic material such as polymers, gels or glues, is guided angiographically or with intravascular ultrasound to insure obliteration of the aneurysm cavity external to the stent lumen. Gradual thrombosis and fibrosis of the aneurysm cavity lead to shrinkage of the aneurysm cavity around the wire/steel, NITENOL™ reinforced aortic wall, which in turn will prevent later rupture of the aneurysm. This safe and effective technique for percutaneous treatment of aortic aneurysms presents very low risk and enables preventive placement of the device in patients not previously considered good candidates for surgery, e.g., patients with small (less than four centimeter) aortic aneurysms or those with significant co-morbidities.

It is therefore an object of the instant invention to provide a device specifically designed for treatment of an aneurysm of the descending aorta or other blood vessels with naturally occurring or traumatic (pseudo aneurysm) arterial bulging with the potential for either rupture or distal embolization. The invention may be used in linear, curved or bifurcated vessels. The invention presents a unique device and method for treating aneurysms particularly when an aneurysm occurs proximal to a bifurcation in a vessel.

It is a further object of the instant invention to provide a device featuring an open or semi-permeable stent design, allowing for secure placement with stent overlap of normal aorta above the renal ostia. The bifurcation segments of the instant invention are deployed across the bifurcation with significant increase in bifurcation segment size and significant overlap with the main stent above the bifurcation allowing for axial stability, which resists axial migration and late disruption. Covered stent grafts with non-permeable coverings predispose to perigraft leakage from branch vessels, which can lead to aneurysm expansion and late rupture, as well as the potential, at least in animal models, of lack of blood flow in the side branches of lumbars with subsequent paraplegia. The open stent design with a semi-permeable covering of the instant invention allows for continued blood flow into the side branches that are immediately opposed to the stent, such as in the lumbar location. Coil, gel or foam embolization of the remaining side branches can be utilized to prevent perigraft leakage such as at the level of the inferior mesenteric artery.

It is a further object of the instant invention to provide a device with a continuous stent backbone that effectively prevents axial migration. The instant device and method are designed to facilitate deployment above the renal arteries without impeding flow into the renal arteries in the case of patients with a short segment of normal aorta below the renal arteries and in whom both iliacs are included in the bifurcation, precluding the need for concomitant vascular surgery.

It is a further object of the instant invention to provide a device utilizing tapered, semi-circular segments to be situated in the main stent and extending into the branch vessels proceeding from the point of bifurcation. The taper of each segment narrows proceeding from the proximal end which is placed in the main stent. The tapered segments thus form a stable union by virtue of their "cork-like" semi-conical configuration since when the segments are deployed in the main stent their wide, semi-circular ends contact each other with the flat end of the semi-circles in contiguity and the outward pressure of the segmental stent expansion maintains the rounded portion of the semi-circles against the walls of the main stent. This pressure, combined with the taper of each segment matching the taper of the distal aorta and exceeding the diameter of the iliac vessels prevents the segments from slipping distally in the stent and/or becoming dislodged. The main stent configuration of the instant invention allows for placement of the initial, large-cell uncovered segment above the renal arteries for axial stability and a continuous stented segment to the bifurcation for further axial stability, which obviates the possibility of independent motion of the iliac branches.

It is a further object of the instant invention to provide an aneurysmal repair device with a long stent segment, a portion of which, with large cell size, permits placement above the origins of the renal arteries for additional axial stability. The entire stent device is intact, therefore, there should be no possibility of axial migration. Additionally, the device of the instant invention is semi-permeable for both side branch continuity (i.e. lumbars), as well as providing access for embolization of the potential space in the aneurysm sac surrounding the main stent. The instant invention described herein includes use of angled guide-wires which will minimize kinking of the legs during deployment.

It is the further object of the instant invention to:
(1) Allow percutaneous insertion and percutaneous suture closure of the arteriotomy due to the lack of a bulky covering of the stent.
(2) Utilize partial covering of the stent which permits blood flow into important side branches, such as the lumbars, which then seal off around their ostia, forming an incorporation into the stent lumen, effectively forming a biologic connection between the stent lumen and the side branch blood vessel(s) without allowing blood into the extra stent aneurysm cavity.
(3) Further utilize the uncovered portion of the stent with large cell size which permits anchoring of the graft above the renals without compromising the blood flow into the renals due to the large cell size of that portion of the stent.
(4) Provide minimal covering, allowing percutaneous placement.
(5) Provide an open space at the superior margin that allows for anchoring above the renals.
(6) Utilize the continuous axial skeleton to prevent axial dislodgment after implant.

The methods of the instant invention utilize a smaller percutaneous entry site, avoidance of side branch occlusion and slow, controlled fibrosis of the aneurysm cavity, reducing the risk for potential complications such as compromise of blood flow to the mesentery and spinal chord, late perigraft leaks and subsequent aneurysm expansion and late rupture.

This safe and effective technique for percutaneous treatment of aortic aneurysms presents very low risk and enables preventive placement of the device in patients note previously considered good candidates for surgery; e.g., patients with small (less than four centimeter) aortic aneurysms or those with significant co-morbidities.

The foregoing and other objects and advantages of the invention will appear from the following description. In the description, reference is made to the accompanying drawings, which form a part hereof, and in which there is shown by way of illustration a preferred embodiment of the invention including novel stent constructions and methods of use hereof. The embodiment that is illustrated in these figures does not necessarily represent the full scope of the invention, however, and reference is made therefore to the claims herein for interpreting the scope of the invention.

BRIEF DESCRIPTION OF THE DRAWINGS

FIG. 2A is a diagrammatic view of the first bifurcation stent of the abdominal aortic stenting and aneurysm exclusion device of FIG. 1A.

FIG. 2B is a diagrammatic view of the second bifurcation stent of the abdominal aortic stenting and aneurysm exclusion device of FIG. 1A.

FIG. 2C is a diagrammatic view of the first and second bifurcation stents abutting each other in the configuration achieved in the abdominal aortic stenting and aneurysm exclusion device of FIG. 1A.

DETAILED DESCRIPTION OF THE INVENTION

Figure 1A:
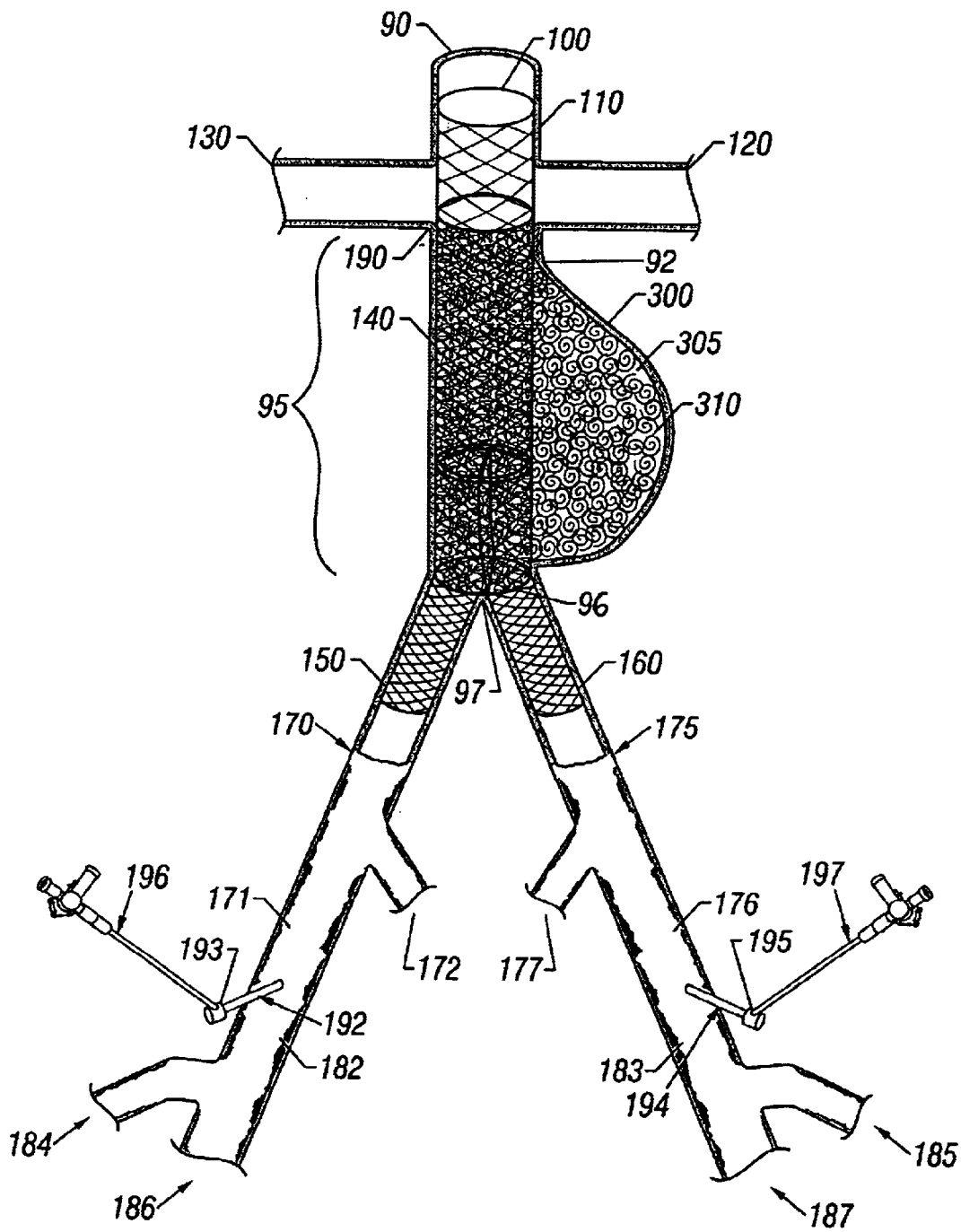
FIG. 1A is a diagram of a preferred embodiment of an abdominal aortic stenting and aneurysm exclusion device composed of main and a first and second bifurcation stent constructed in accordance with the teachings of the present invention shown in place in the abdominal aorta.
Figure 6A:
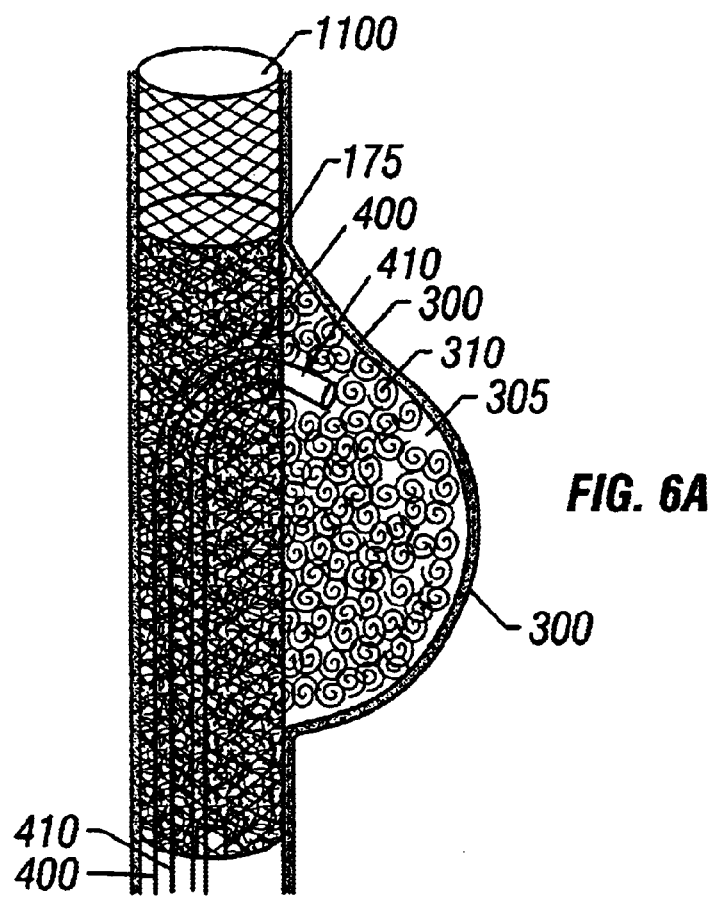
FIG. 6A is a diagram of a second embodiment of the instant invention depicting a stenting and aneurysm exclusion device comprising a main stent and means for introduction of embolization coils into an aneurysm in an essentially linear blood vessel.
Figure 6B:
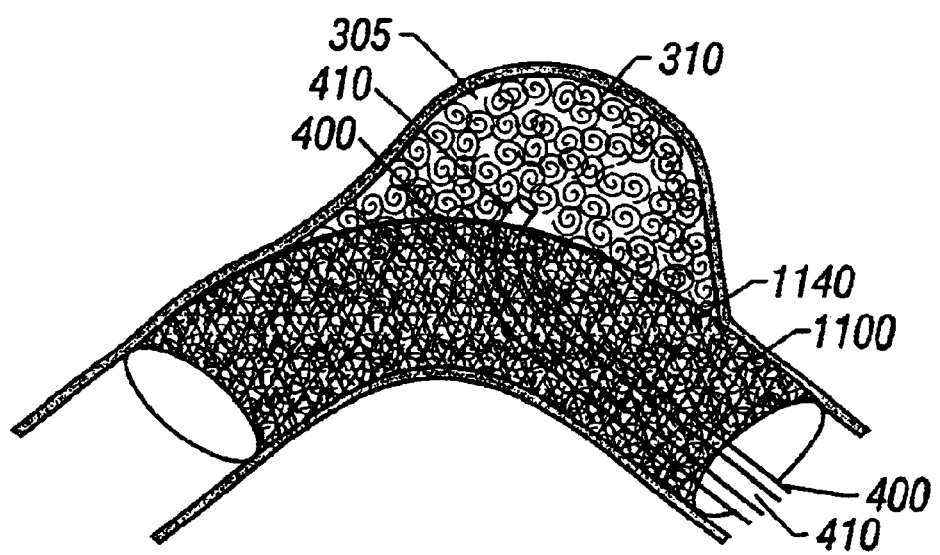
FIG. 6B is a diagram of a second embodiment of the instant invention depicting a stenting and aneurysm exclusion comprising a main stent and means for introduction of embolization coils into an aneurysm in a curved blood vessel.

Referring now to the various figures depicting the invention where like reference numerals refer to like parts, there is shown at 1 in FIG. 1A, at 2 in FIG. 6A and at 3 in FIG. 6B respective embodiments of an endoluminal prosthesis comprising a stent graft which carries a prosthetic layer of fabric tufts, foam or other semi-permeable material to be used in treatment of an aneurysm by removing the pressure on a weakened part of the aneurysmally dilated wall of an artery so as to reduce the risk of embolism or rupture of the distended wall of the aneurysm. The embodiments of the invention may be used in either bifurcated or non-bifurcated vessels.

Figure 1C:
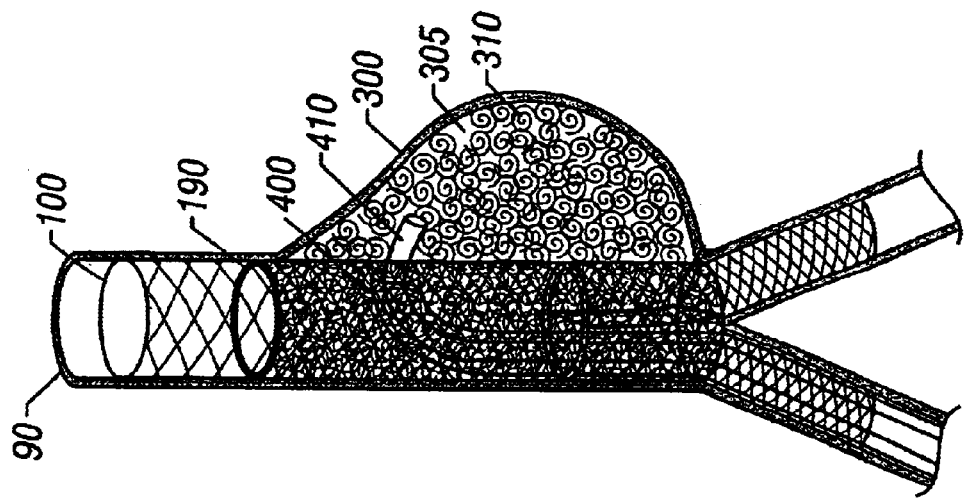
FIG. 1C is a diagram showing the use of abdominal aortic stenting and aneurysm exclusion of FIG. 1A being used with an angiographic catheter for delivery of embolization coils, foam, gel or glue to the aneurysm cavity.
Figure 1B:
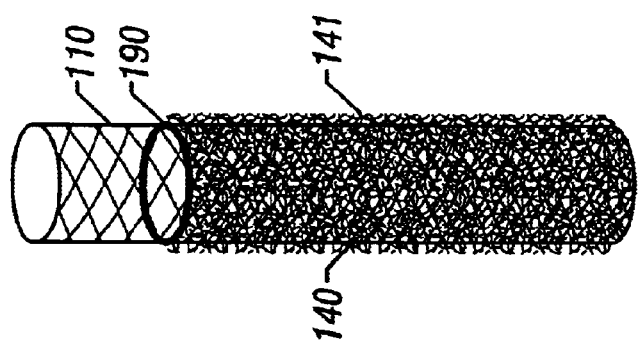
FIG. 1B is a diagrammatic view of the main stent of the abdominal aortic stenting and aneurysm exclusion device of FIG. 1A showing the internal wire mesh, radio-opaque marker band and outer tufts on the stent.

FIG. 1A depicts the use of the invention in a bifurcated vessel with an aneurysm 305. The depicted location of the neck of the aneurysm 92 is representative only and may vary from case to case. FIGS. 6A and 6B illustrate the use of the invention in non-bifurcated vessels with aneurysms 305. FIG. 1A shows the cylindrical main stent 100 in place in the aorta 90. The main stent 100 is comprised of an upper portion 110 constructed of a mesh of intersecting flexible wires or etched metal tubing with mesh cell size ranging from two (2) to four and one-half (4½) millimeters, allowing full, unrestricted blood flow into the renal arteries and a lower portion constructed of mesh of the same intersecting flexible wires or etched metal tubing 140 with smaller mesh cell size ranging from one and one-half (1½) to three (3) millimeters. The main stent 100 ranges in length from seven (7) to twelve (12) centimeters with the upper portion 110 ranging in length from four (4) to eight (8) centimeters and the lower portion 140 ranging in length from three (3) to eight (8) centimeters. The cross-sectional diameter of the main stent 100 ranges from twenty (20) to thirty (30) millimeters. Cell size refers to the size of the spaces in the mesh pattern formed by the metal comprising the stent wall. The border between the upper large cell size 110 and lower, small cell size 140 portion of the main stent 100 is demarcated by a radio-opaque marker band 190. The total length of the main stent is chosen to extend a sufficient length so that the ends of the main stent 100 extend past the section of the vessel containing the aneurysm. In the case of aneurysms extending to the juncture of bifurcated vessels, the small cell size portion 140 will extend from the level of the lower margin of the right 130 and left 120 renal arteries to the aortic bifurcation 97. The main stent 100 section below the marker band 190 which is also termed the small cell size portion 140 is covered with biocompatible polymeric foam or DACRON®/other material 141 (FIG. 1B) which promotes fibrin deposition and subsequent endothelialization along the stent surfaces. This coating 141 is semi-permeable which allows trans-stent insertion of an angiographic or embolic material delivery catheter 410. The semi-permeability of the coating 141 similarly allows insertion of thrombogenic material (coils, foam, gel, glue, etc.) 310 from the inner lumen of the stent through the stent cells and into the aneurysm cavity 305 using an angiographic or embolic material delivery catheter 410 as shown in FIGS. 1C, 6A, or 6B.

Additional features depicted in FIG. 1A include the infra renal aorta 95, the right 150 and left 160 iliac bifurcation stents, the right 170 and left 175 common iliac arteries, the right 171 and left 176 external iliac arteries, the right 172 and left 177 internal iliac arteries, the right 182 and left 183 common femoral arteries, the right 184 and left 185 profundus femori the right 186 and left 187 superficial femoral arteries, and the right 192 and left 194 common vascular access sheaths.

The main stent 100 is inserted over a guiding wire 250. It is initially housed in a stent delivery device 200 which allows it to maintain a small crossing profile, permitting it to be inserted percutaneously through a vascular access hemostatic sheath 192 or 194 that is provided with hemostatic seals 193 and 195 and left 196 and right 197 side arms and stopcocks. Once the stent-containing delivery device 200 is positioned within a vessel, such as the abdominal aorta, with placement so that the radio-opaque marker band 190 on the stent is positioned just at the lower margin of the renal arteries 120 and 130, the inner stent delivery tube 235 is fixed with respect to the patient while the outer sheath 230 is retracted. This effectively uncovers the main stent 100, allowing it to expand and oppose the normal aorta above the renal arteries 120, 130 and subsequently the aneurysm neck 92, shown in FIG. 1A immediately below the renal arteries 120 or 130, throughout its fill extension, to a position just above the aortic bifurcation 97.

The delivery wire 250 is left in position while the stent delivery system 200 is removed. In the case of bifurcated vessels, a second deliver, wire 251 is then introduced via the left femoral artery access sheath 194. The two delivery wires 250 and 251 are essentially parallel in the lumen of the aorta and diverge at the bifurcation point 97 with each delivery wire descending into the respective branching vessels. In order to achieve a continuous seal of the endovascular lumen and effectively exclude the aneurysm cavity in bifurcated vessels, two sectional (bifurcation) stent delivery sheaths 201 right 150 and left 160 iliac sectional (bifurcation) stents are advanced simultaneously over the delivery guide-wires 250 and 251. The sectional (bifurcation) stents 150 and 160 have first, frustro-conically tapered proximal portions constructed with a large mesh size and second cylindrical distal portions constructed with a smaller mesh size than the proximal portions. The mesh of the sectional stents is constructed of flexible wires or etched metal tubing defining a cell size in the proximal portions in the range from two (2) to four and one-half (4.5) millimeters and in the distal portions in the range from one and one-half (1.5) to three (3) millimeters. The sectional (bifurcation) stents 150 and 160 range in total length from eight (8) to twelve (12) centimeters with the distal cylindrical portions, ranging in length from three (3) to five (5) centimeters. The dimension of the widest part of the semi-circular shape of the proximal ends of the first 142 and the second 147 sectional (bifurcation) stents ranges from twenty (20) to thirty (30) millimeters with the tapered proximal portions (above the radio-opaque marker band 149) ranging in length from five (5) to seven (7) centimeters. The portions of the proximal portions of the sectional stents are covered with a semipermeable coating ranging in length from one (1) to two (centimeters). The diameter of the distal portions of the sectional (bifurcation) stents 150 and 160 range from twelve (12) to eighteen (18) millimeters.

The delivery wire 250 is left in position while the stent delivery system 200 is removed. In the case of bifurcated vessels, a second deliver, wire 251 is then introduced via the left femoral artery access sheath 194. The two delivery wires 250 and 251 are essentially parallel in the lumen of the aorta and diverge at the bifurcation point 97 with each delivery wire descending into the respective branching vessels. In order to achieve a continuous seal of the endovascular lumen and effectively exclude the aneurysm cavity in bifurcated vessels, two sectional (bifurcation) stent delivery sheaths 201 right 150 and left 160 iliac sectional (bifurcation) stents are advanced simultaneously over the delivery guide-wires 250 and 251. The sectional (bifurcation) stents 150 and 160 have first, frustro-conically tapered proximal portions constructed with a large mesh size and second cylindrical distal portions constructed with a smaller mesh size than the proximal portions. The mesh of the sectional stents is constructed of flexible wires or etched metal tubing defining a cell size in the proximal portions in the range from two (2) to four and one-half (4.5) millimeters and in the distal portions in the range from one and one-half (1.5) to three (3) millimeters. The sectional (bifurcation) stents 150 and 160 range in total length from eight (8) to twelve (12) centimeters with the distal cylindrical portions, ranging in length from three (3) to five (5) centimeters. The dimension of the widest part of the semi-circular shape of the proximal ends of the first 142 and the second 147 sectional (bifurcation) stents ranges from twenty (20) to thirty (30) millimeters with the tapered proximal portions (above the radio-opaque marker band 149) ranging in length from five (5) to seven (7) centimeters. The portions of the proximal portions of the sectional stents are covered with a semipermeable coating ranging in length from one (1) to two (centimeters). The diameter of the distal portions of the sectional (bifurcation) stents 150 and 160 range from twelve (12) to eighteen (18) millimeters.

The medial radio-opaque marker beads 210 and 211 are approximated on both sheaths by careful application of torque on the stent delivery devices 200 or 201 with fluoroscopic guidance. Subsequently, two operators independently fix the inner stent delivery tubes 235 on each bifurcation stent and the delivery sheaths 230 are withdrawn simultaneously in a continuous motion, allowing deployment of the bifurcation stents simultaneously with the flat or non-curvilinear portion 142 and 147 of the semi-circular wall of each bifurcation stent approximated in the middle of the main stent. Thus, the semicircular openings 143 and 146 join together, forming an optimal entrance of the blood flow into each iliac stent portion. The radio-opaque marker band on the bifurcation stent 149 is positioned at the aortic bifurcation prior to de-sheathing the iliac stents. As the sheaths are retracted simultaneously, the semi-circular openings expand against one another, with the lateral margins compressing against the main stent border and the medial, flat or non-curvilinear portions of the semi-circularly-shaped ends 142, 147 compressing against one another. The simultaneous compression of the bifurcation stents inwardly against each other and outwardly against the inside wall of the main stent combined with the bifurcation stents' tapered conformation serve to affirmatively retain the bifurcation stents in position at the bifurcation and to resist dislocation, dislodgment or displacement.

The combination of semi-permeable coating 155 and the configuration of the stents allows for the formation of an impermeable hemostatic seal between the main stent 100 and the bifurcation stent lumens 150, 160. Thus, the risk of an endo leak at the bifurcation is effectively eliminated.

Figure 5A:
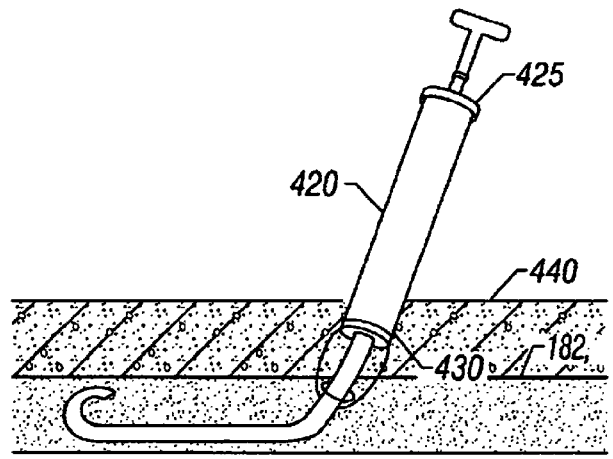
FIG. 5A is a schematic diagram showing the implementation of arteriotomy closure strategies with sutures.
Figure 5B:
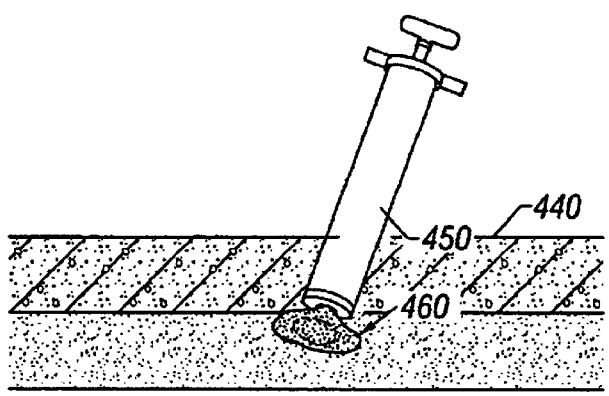
FIG. 5B is a schematic diagram showing the implementation of arteriotomy closure strategies with collagen plugs or gel.

After successful delivery of the main 100 and/or bifurcation stents 150, 160, an angiographic guide catheter 400 is advanced via the vascular access sheath 192, superior to the bifurcation stent semi-circular openings 143 and 146 positioned in the small cell portion 140, immediately adjacent to the aneurysm cavity. Subsequently, an angiographic catheter 410 is inserted through the angiographic guide catheter 400 and advanced through the main stent wall 100 into the aneurysm cavity 305. Its position is confirmed within the aneurysm cavity by injection of radio-opaque contrast and x-ray imaging. Subsequently, thrombogenic material (coils, foam, gel, glue, etc. 310) is injected into the aneurysm cavity 305 to stimulate thrombosis of the material external to the main 100 and bifurcated stent 150 and 160. After successful obliteration of the aneurysm cavity 305 using thrombogenic material 310, the sheathes 192, 194 are removed and the access sites are closed, utilizing suture devices 425 and suture 430 (FIG. 5A) or collagen plug devices 450 and collagen plugs 460 (FIG. 5B) in the standard fashion.

Detailed Description of the Procedure

In the preferred embodiment, an operator achieves vascular access percutaneously via the right 182 and left 183 common femoral arteries and insert size twelve (12) french standard angiographic sheaths 192 and 194. Control angiography is performed on the infra renal abdominal aorta 95 or other vessel with an aneurysm using standard techniques for guidance of the aneurysm stent implantation procedure.

A marker delivery wire 250 is inserted through the angiographic sheath 192 in the right common femoral artery 182 and positioned with the angle marker bead 260 positioned at the aortic bifurcation 97.

The distance between the lower most renal artery 120 or 130 and the aortic bifurcation 97 is noted using the marker delivery wire 250 and an appropriately sized main stent 100 is chosen for delivery.

The main stent delivery system 200 containing the main stent 100 is inserted with the distal radio-opaque stent fixation plug 225 at the leading end and hemostatic seal 231 at the trailing end and then advanced through the right iliac angiographic sheath 192 over the NITENOL™ marker delivery wire 250 and positioned with the radio-opaque marker band 190 just below the lower most renal artery 120 or 130, whichever is lowest, and the radio-opaque fixation disk 236 at the aorta bifurcation 97.

The main stent delivery sheath 230 is retracted, allowing the main stent 100 to expand and be deployed in the abdominal aorta 95.

The main stent delivery system 200 is removed over the right iliac marker delivery wire 250, which is left in position.

The left iliac marker delivery wire 251 is then advanced via the left common femoral hemostatic sheath 194 through the external and common iliacs and up the abdominal aorta 95 inside the main stent 100, thereupon positioning the angle marker bead 261 at the aortic bifurcation 97.

One bifurcation sheath deliver device 201 containing one bifurcation stent 150 is advanced over the right iliac guide-wire 250 and positioned so that the radio-opaque marker band 149 is at the aortic bifurcation and that the medial marker beads 210 and 220 are positioned medially in the aorta 95, just above the aortic bifurcation 97. When sheath 201 is advanced to this position, marker beads 211 and 221 are proximate the lower margin 96 of main stent 100.

A second, contra-lateral bifurcation stent 160 is advanced over the marker delivery wire 251 via the sheath 194 in the left femoral artery 183 into a position opposing the previously positioned right-sided iliac stent 150. The marker band 149 is positioned at the aortic bifurcation 97 and the radio-opaque marker beads 210 and 220 on the bifurcation delivery sheath 200 are immediately opposed to those beads on the sheath delivery system 200 on the ipsilateral side 150. The stent covering sheaths 230 and 232 are then simultaneously withdrawn over the inner stent delivery tubes 235 and 237 by two operators while the inner stent delivery tubes 235 and 237 are fixed in position, assuring that no axial migration occurs during stent deployment. Withdrawing stent covering sheaths 230 and 232 allows the flat side of the tapered semi-circular bifurcation segments 142 and 147 on each side to oppose one another, forming a seal in the distal portion of the aorta 92 against each bifurcation stent medially and circumferentially against the main stent 100. The iliac limbs 150 and 160 will then extend into the iliac vessels 170 and 175 bilaterally.

Once the iliac stents 150 and 160 are successfully deployed, the iliac bifurcation stent delivery systems 200 and 201 are withdrawn. Subsequently, a standard angiographic right Judkins guiding catheter 400 is advanced over one of the stent delivery wires into the aorta 95 and positioned just opposite the main aneurysm sac 305. Following this positioning maneuver, the angiographic catheter 410 is advanced over the standard angiographic guide-wire into the aneurysm cavity 305. Thrombogenic material 310 is then delivered via this standard angiographic guiding catheter 410 into the aneurysm cavity 305 in an amount sufficient to obliterate the residual aneurysm 300 surrounding the main stent 100.

Alternatively, prior to placement of the iliac stents 150 and 160, a separate angiographic material delivery catheter 410 is placed in the aneurysm sac 305 adjacent to the main stent 100 and positioned so that thrombogenic material 310 can be delivered external to the stent 100. After successful delivery of thrombogenic material 310 into the aneurysm sac 305, the catheter 410 is withdrawn and the second marker delivery wire 251 could be replaced through the angiographic sheath 194 for delivery of the iliac stents 150 and 160.

Following angiographic confirmation of successful obliteration of the aneurysm cavity 305, the arteriotomy sites 440 are closed percutaneously using percutaneous closure devices (either suture based devices 420 or collagen plug type devices 450) to minimize risk of hematoma formation and/or blood loss.

The prosthetic stent combination, delivery apparatus and methods described above are particularly useful in treating an abdominal aortic aneurysm in a bifurcated vessel according to the present invention. Other diseases and alternative embodiments of the prosthesis and delivery method will now be described. The parallels between the alternatives and the preferred embodiment will be apparent to one skilled in the art.

Referring to FIGS. 6A and 6B, preferred embodiments of non-bifurcated stents constructed in accordance with the teachings of the present invention for treatment of an aneurysm in a non-bifurcated straight or curved vessel segment are shown at reference numerals 1100. Each of the non-bifurcated stents 1100 are comprised of a flexible mesh or etched tubular material with small cell size. Cell size refers to the size of the spaces in the mesh pattern formed by the metal comprising the stent wall. The total length of the non-bifurcated stent is chosen to extend a sufficient length so that the ends of the stent extend past the section of the vessel containing the aneurysm. The non-bifurcated stent 1100 is covered with biocompatible polymeric foam or DACRON® tufts/other semi-permeable material which promotes fibrin deposition and subsequent endothelialization along the stent surfaces. This coating is semi-permeable which allows trans stent insertion of an angiographic or embolic material delivery catheter 410. The semipermeability similarly allows insertion of thrombogenic material (coils, foam, gel, glue, etc. 310, as may be seen in FIGS. 1A or 1C) from the inner stent lumen through the stent cells into the aneurysm cavity 305.

Figure 3:
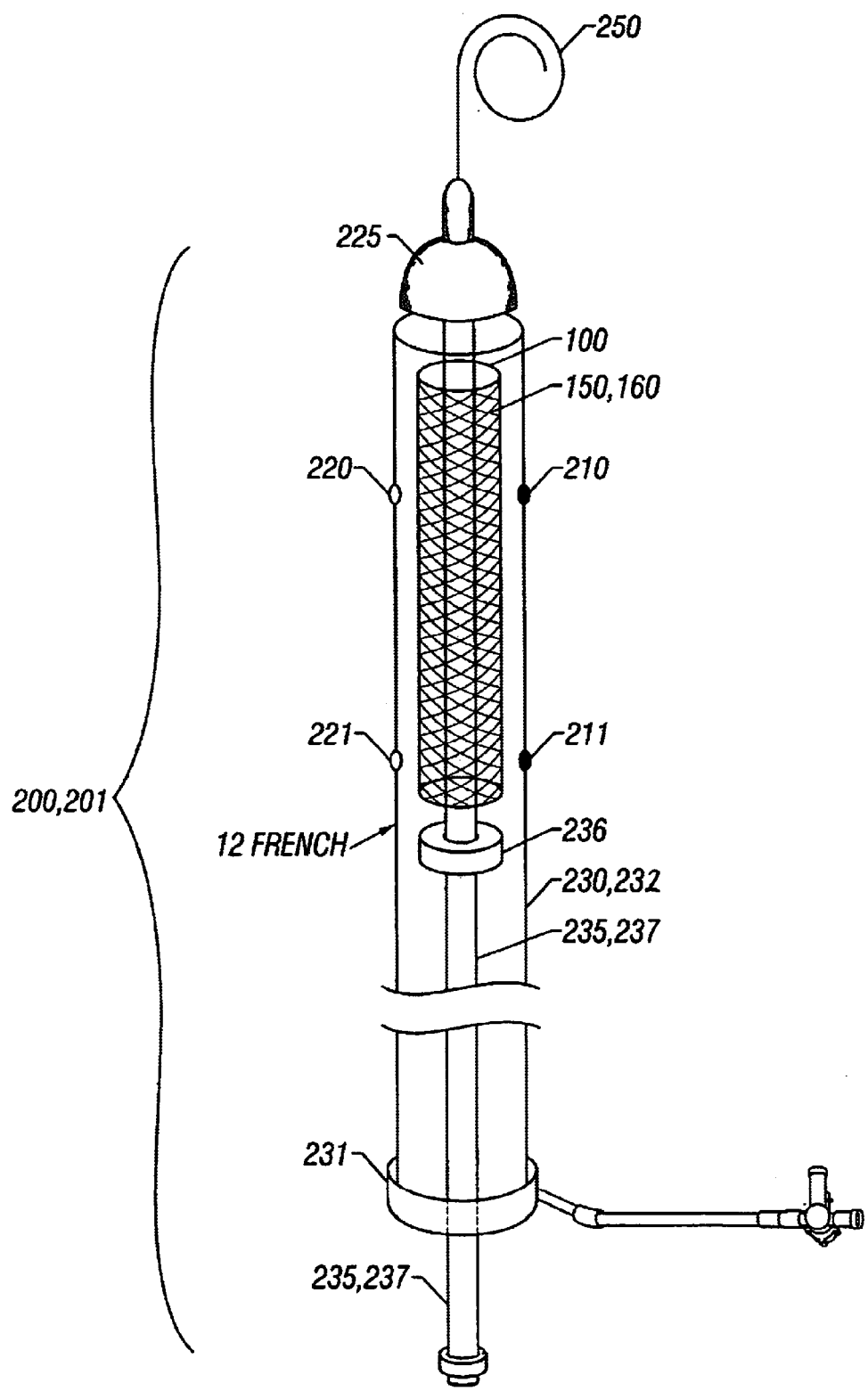
FIG. 3 is a schematic view of a bifurcation sheath delivery device for the abdominal aortic stenting and aneurysm exclusion device shown in FIG. 1A.
Figure 4:
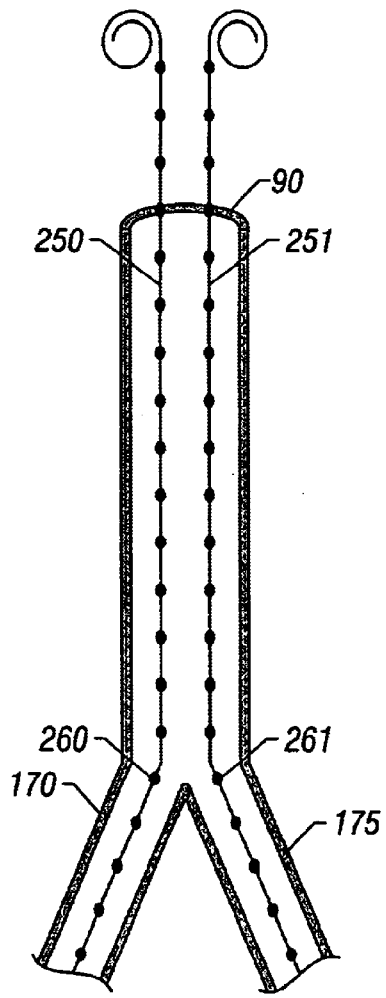
FIG. 4 is a schematic view of the placement of the abdominal aortic stenting and aneurysm exclusion device marker delivery wires.

The non-bifurcated stent 1100 is inserted over a guiding wire 250 as shown in FIG. 3. It is initially housed in a stent delivery device 200 which allows it to maintain a small crossing profile, permitting it to be inserted percutaneously through a vascular access hemostatic sheath 192. Once the stent-containing delivery device 200 is positioned within a vessel such as the descending thoracic aorta with placement so that the ends of the stent are positioned well on either side of the aneurysm cavity 305, the inner stent delivery tube 235 is fixed with respect to the patient while the outer sheath 230 is retracted. This effectively uncovers the non-bifurcated stent 1100 allowing it to expand and oppose the normal vessel on either side of the aneurysm cavity 305. The delivery wire 250 is left in position while the stent delivery system 200 is removed.

After successful delivery of the non-bifurcated stent 1100, an angiographic guide catheter 400 is advanced via the vascular access sheath 192 and approximated against the medial non-bifurcated stent wall 1140, immediately adjacent to the aneurysm cavity. Numbering in the 1000's is used for the distinct non-bifurcated stents but not for the aneurysm related structure or the delivery apparatus. Subsequently, an angiographic catheter 410 is inserted through the angiographic guide catheter 400 and advanced through non-bifurcated stent 1100 into the aneurysm cavity 305. Its position is confirmed within the aneurysm cavity by injection of radio-opaque contrast and x-ray imaging. Subsequently, thrombogenic material (coils, foam, gel, glue, etc. 310) is injected into the aneurysm cavity 305 to stimulate thrombosis of the material external to the non-bifurcated stent 1100. After successful obliteration of the aneurysm cavity 305 using thrombogenic material 310, the access sites are closed, utilizing suture devices 425 and suture 430 or collagen plug devices 450 and collagen plugs 460 in the standard fashion.

Although described in terms of the presently preferred embodiments shown in the accompanying figures, those skilled in the art who have the benefit of this disclosure will recognize that certain changes can be made to the specifics thereof that do not change the manner in which the component parts thereof function to achieve their intended result. All such changes which do not depart from the spirit of the invention are intended to fall within the scope of the following non-limiting claims.

What is claimed is:

1. An apparatus for repair of an aneurysm in bifurcated blood vessels comprising:
   a main stent with a first, proximal portion and a second, distal portion, said proximal portion constructed with large mesh cell size and said distal portion constructed with smaller mesh cell size than said proximal portion;
   first and second sectional stents with first, frustro-conically tapered, proximal portions and second cylindrical distal portions, said proximal portions constructed with large mesh size and with semi-circular, proximal ends of said proximal portions, said distal portions constructed with smaller mesh size than said proximal portions, wherein said sectional stents fit contiguously into said distal portion of said main stent thereby completely filling said main stent;
   means for inserting said main stent and said first and second sectional stents into a bifurcated blood vessel at or near the bifurcation in the vessel; and
   means for fitting said first and second sectional stents into said main stent within the bifurcated vessel wherein a portion of said main stent is proximate to an aneurysm in the vessel wall.

2. The apparatus of claim 1 wherein said mesh of said proximal portions of said main stent and said first and second sectional stents are constructed of intersecting flexible wires defining cell size in the range from two (2) to four and one-half (4.5) millimeters and said mesh of said distal portions of said main stent and said first and second sectional stents are constructed of intersecting flexible wires or etched metal tubing defining a cell size in the range from one and one-half (1.5) to three (3) millimeters.

3. The apparatus of claim 1 wherein said main stent ranges in length from seven (7) to twelve (12) centimeters, with said first, proximal portion ranging in length from four (4) to eight (8) centimeters and said second, distal portion ranging in length from three (3) to eight (8) centimeters.

4. The apparatus of claim 1 wherein said main stent has a cross sectional diameter ranging from twenty (20) to thirty (30) millimeters and the dimension of the widest part of the semi-circular shape of the proximal ends of the first and second sectional stents ranges from twenty (20) to thirty (30) millimeters.

5. The apparatus of claim 1 wherein the sectional stents range in total length from eight (8) to twelve (12) centimeters with the tapered proximal portions ranging in length from five (5) to seven (7) centimeters, with the distal cylindrical portions ranging in length from three (3) to five (5) centimeters.

6. The apparatus of claim 1 additionally comprising a semi-permeable coating of said main and sectional stents.

7. The apparatus of claim 1 wherein said means for inserting said main stent and said first and second sectional stents into a bifurcated blood vessel comprises:
   a first delivery guidewire describing an obtuse angle substantially similar to the angle described by the walls of the bifurcated vessel, constructed with a plurality of radio-opaque marker beads along the length of said delivery guidewire, with a marker bead located at the apex of the bend in said delivery guidewire, said delivery guidewire housed in a first stent deliver device insertable percutaneously through a vascular access hemostatic sheath;
   a second delivery guidewire describing an obtuse angle substantially similar to the angle described by the walls of the bifurcated vessel, constructed with a plurality of radio-opaque marker beads along the length of said delivery guidewire, with a marker bead located at the apex of the bend in said delivery guidewire, said deliver guidewire housed in a second stent delivery device insertable percutaneously through a vascular access hemostatic sheath;
   an inner stent delivery tube;
   an outer delivery sheath; and
   first and second cylindrical bifurcation stent delivery sheaths, each of said bifurcation stent delivery sheaths constructed with a first and second array of radio-opaque markers on the outside thereof, each array with a proximal and a distal marker, said markers being arrayed along a longitudinal axis of said bifurcation stent delivery sheath with the distal marker of the first array opposite the distal marker of the second array and the proximal marker of the first array opposite the proximal marker of the second array.

8. The apparatus of claim 1 wherein said main stent and said first and second sectional stents are comprised of memory retentive material compressible for insertion into a bifurcated blood vessel in a patient and expandable into a configuration wherein said main stent contacts the walls of said vessel and said first and second sectional stents are insertable and expandable into said main stent to fully occupy the lumen of said main stent and with the proximal ends of said first and second sectional stents further expandable into contact against each other, said contact ensuring said first and second sectional stents are positioned with distal portions extending into the branches of said bifurcation and resisting displacement or subsequent disassociation of the sectional stents from the main stent.

\* \* \* \* \*